United States Patent
Stoyanov et al.

(10) Patent No.: US 10,527,524 B2
(45) Date of Patent: Jan. 7, 2020

(54) METHOD OF INSPECTING COMPONENT SURFACE WITH MARKING MEDIA

(71) Applicant: UNITED TECHNOLOGIES CORPORATION, Farmington, CT (US)

(72) Inventors: Pantcho Stoyanov, Woodland Hills, CA (US); Elizabeth V. Favela, El Paso, TX (US)

(73) Assignee: United Technologies Corporation, Farmington, CT (US)

( * ) Notice: Subject to any disclaimer, the term of this patent is extended or adjusted under 35 U.S.C. 154(b) by 186 days.

(21) Appl. No.: 15/334,452

(22) Filed: Oct. 26, 2016

(65) Prior Publication Data

US 2018/0113053 A1 Apr. 26, 2018

(51) Int. Cl.
*G01M 15/14* (2006.01)

(52) U.S. Cl.
CPC ......... *G01M 15/14* (2013.01); *F05D 2230/72* (2013.01)

(58) Field of Classification Search
CPC ............................ G01M 15/14; F05D 2230/72
See application file for complete search history.

(56) References Cited

U.S. PATENT DOCUMENTS

| | | | |
|---|---|---|---|
| 1,978,716 A | 10/1934 | Morehouse | |
| 2,330,257 A | 9/1943 | Bailey | |
| 3,421,223 A | 1/1969 | Stark | |
| 3,731,687 A | 5/1973 | Glassman | |
| 3,813,781 A | 6/1974 | Forgione | |
| 3,959,881 A | 6/1976 | Kokal, Jr. | |
| 4,547,155 A | 10/1985 | Adler | |
| 5,326,261 A | 7/1994 | Rains | |
| 5,395,239 A * | 3/1995 | Komatsu | A61C 19/05 433/68 |
| 5,676,647 A | 10/1997 | Cimber | |
| 5,704,759 A * | 1/1998 | Draskovich | F01D 11/12 415/170.1 |
| 5,935,407 A * | 8/1999 | Nenov | C23C 28/00 205/183 |
| 5,941,150 A | 8/1999 | Kropf et al. | |
| 6,592,540 B2 | 7/2003 | DeCarlo | |
| 7,190,440 B2 * | 3/2007 | Ng | G01L 1/247 356/32 |
| 7,810,447 B2 | 10/2010 | Manos et al. | |
| 8,219,367 B2 * | 7/2012 | Iwata | B24C 5/06 703/6 |

(Continued)

FOREIGN PATENT DOCUMENTS

| | | |
|---|---|---|
| EP | 2233600 A1 | 9/2010 |
| EP | 2962844 A2 | 1/2016 |

OTHER PUBLICATIONS

European Search Report for EP Application No. 17196025.5 dated Mar. 23, 2018.

*Primary Examiner* — Freddie Kirkland, III
(74) *Attorney, Agent, or Firm* — Carlson, Gaskey & Olds, P.C.

(57) ABSTRACT

A method of evaluating the quality of a surface on a component comprises the steps of (a) contacting a surface of a component with a media and imprinting qualities of the surface with the media; and (b) evaluating the imprint to determine the quality of the surface of the component.

15 Claims, 4 Drawing Sheets

(56) References Cited

U.S. PATENT DOCUMENTS

| | | | | |
|---|---|---|---|---|
| 2004/0050173 A1* | 3/2004 | Ng | .......................... | G01L 1/247 |
| | | | | 73/800 |
| 2009/0222244 A1* | 9/2009 | Iwata | ........................ | B24C 1/00 |
| | | | | 703/2 |
| 2010/0242477 A1* | 9/2010 | Duval | ........................ | C23C 4/18 |
| | | | | 60/645 |
| 2016/0003092 A1* | 1/2016 | Chamberlain | .......... | C04B 41/85 |
| | | | | 428/331 |
| 2017/0101883 A1* | 4/2017 | Chamberlain | .......... | C04B 41/85 |
| 2017/0362952 A1* | 12/2017 | Stoyanov | .................. | F01D 5/02 |

* cited by examiner

METHOD OF INSPECTING COMPONENT SURFACE WITH MARKING MEDIA

BACKGROUND OF THE INVENTION

This application relates to a method of inspecting whether a surface of a component needs repair by imprinting the surface onto a marking media.

Gas turbine engines are known and typically include a fan delivering air into a bypass duct as bypass air and further into a compressor. Air in the compressor is compressed and then delivered into a combustor where it is mixed with fuel and ignited. Products of this combustion pass downstream over turbine rotors driving them to rotate. It is desirable to maintain tight clearances between a radially outer portion of blades rotating with both the compressor and turbine rotors and outer housings or static structure.

Thus, it is known to put an abradable seal radially outwardly of the blades in a compressor and turbine section. The outer tips of the blades may be provided with an abrasive surface to wear into the abradable seal. In particular, abrasive surfaces are applied to the radially outer portion of the compressor blades.

The abrasive surfaces wear and eventually need to be recoated. This is a procedure that would desirably be limited as it will typically require removal of the blade, and the abrasive coatings themselves are expensive. Still, the abrasive materials are recoated periodically, without regard to actual need.

SUMMARY OF THE INVENTION

In a featured embodiment, a method of evaluating the quality of a surface on a component comprises the steps of (a) contacting a surface of a component with a media and imprinting qualities of the surface with the media; and (b) evaluating the imprint to determine the quality of the surface of the component.

In another embodiment according to the previous embodiment, the surface of the component includes a plurality of particles and the quality includes whether the particles have worn such that they should be replaced.

In another embodiment according to any of the previous embodiments, the component is a blade for a gas turbine engine.

In another embodiment according to any of the previous embodiments, the particles are abrasive particles on a rotating blade in a gas turbine engine.

In another embodiment according to any of the previous embodiments, the media includes a marking paper.

In another embodiment according to any of the previous embodiments, the marking paper passes an imprint from the surface onto a second piece of paper.

In another embodiment according to any of the previous embodiments, a size of an average imprint on the second paper is evaluated to determine whether the particles should be replaced.

In another embodiment according to any of the previous embodiments, a percentage of mark on the second piece of paper per unit area of the paper is compared to a limit to identify whether the particles should be replaced.

In another embodiment according to any of the previous embodiments, a size of an average imprint is evaluated to determine whether the particles should be replaced.

In another embodiment according to any of the previous embodiments, a percentage of mark per unit area is compared to a limit to identify whether the particles should be replaced.

In another embodiment according to any of the previous embodiments, the particles are abrasive particles on a rotating blade in a gas turbine engine.

In another embodiment according to any of the previous embodiments, an absence of particles is also identified as part of the quality determination.

In another embodiment according to any of the previous embodiments, an imprint from the media on the particles is evaluated to make the quality determination.

In another embodiment according to any of the previous embodiments, the media includes a marking paper.

In another embodiment according to any of the previous embodiments, a size of an average imprint is evaluated to determine whether the particles should be replaced.

In another embodiment according to any of the previous embodiments, a percentage of mark per unit is compared to a limit to identify whether the particles should be replaced.

In another embodiment according to any of the previous embodiments, the method is performed after the component is resurfaced.

In another embodiment according to any of the previous embodiments, a gauge is utilized to ensure a controllable force provides a contact of step (a).

In another embodiment according to any of the previous embodiments, the size of the average imprint is evaluated to determine whether the particles should be replaced.

In another embodiment according to any of the previous embodiments, a percentage of mark per unit area of the paper is compared to a limit to identify whether the particles should be replaced.

These and other features may be best understood from the following drawings and specification.

DETAILED DESCRIPTION

Figure 1A:
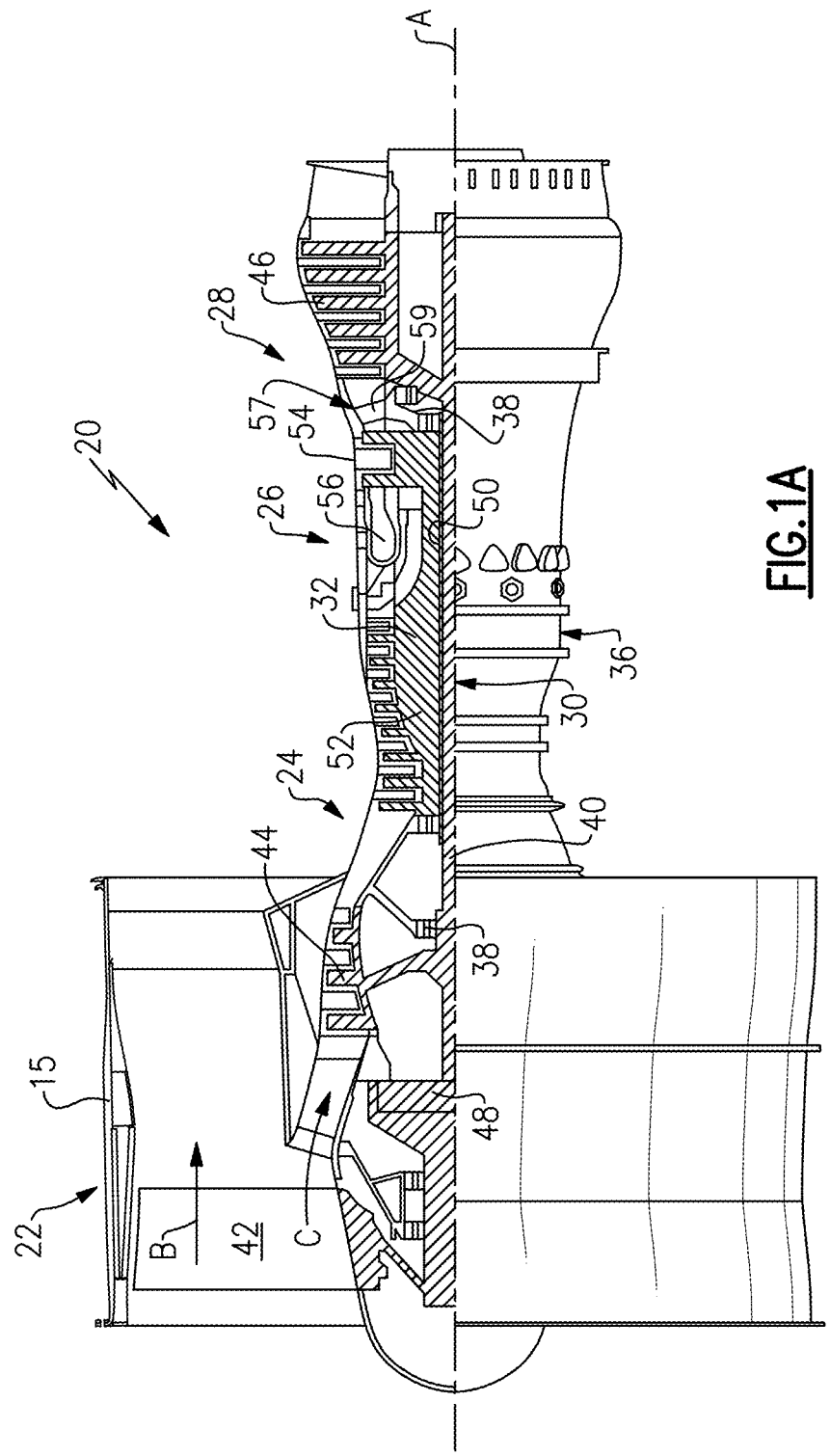
FIG. 1A schematically shows a gas turbine engine.

FIG. 1A schematically illustrates a gas turbine engine 20. The gas turbine engine 20 is disclosed herein as a two-spool turbofan that generally incorporates a fan section 22, a compressor section 24, a combustor section 26 and a turbine section 28. Alternative engines might include an augmentor section (not shown) among other systems or features. The fan section 22 drives air along a bypass flow path B in a bypass duct defined within a nacelle 15, while the compressor section 24 drives air along a core flow path C for compression and communication into the combustor section 26 then expansion through the turbine section 28. Although depicted as a two-spool turbofan gas turbine engine in the disclosed non-limiting embodiment, it should be understood that the concepts described herein are not limited to use with two-spool turbofans as the teachings may be applied to other types of turbine engines including three-spool architectures.

The exemplary engine 20 generally includes a low speed spool 30 and a high speed spool 32 mounted for rotation about an engine central longitudinal axis A relative to an engine static structure 36 via several bearing systems 38. It should be understood that various bearing systems 38 at various locations may alternatively or additionally be provided, and the location of bearing systems 38 may be varied as appropriate to the application.

The low speed spool 30 generally includes an inner shaft 40 that interconnects a fan 42, a first (or low) pressure compressor 44 and a first (or low) pressure turbine 46. The inner shaft 40 is connected to the fan 42 through a speed change mechanism, which in exemplary gas turbine engine 20 is illustrated as a geared architecture 48 to drive the fan 42 at a lower speed than the low speed spool 30. The high speed spool 32 includes an outer shaft 50 that interconnects a second (or high) pressure compressor 52 and a second (or high) pressure turbine 54. A combustor 56 is arranged in exemplary gas turbine 20 between the high pressure compressor 52 and the high pressure turbine 54. A mid-turbine frame 57 of the engine static structure 36 is arranged generally between the high pressure turbine 54 and the low pressure turbine 46. The mid-turbine frame 57 further supports bearing systems 38 in the turbine section 28. The inner shaft 40 and the outer shaft 50 are concentric and rotate via bearing systems 38 about the engine central longitudinal axis A which is collinear with their longitudinal axes.

The core airflow is compressed by the low pressure compressor 44 then the high pressure compressor 52, mixed and burned with fuel in the combustor 56, then expanded over the high pressure turbine 54 and low pressure turbine 46. The mid-turbine frame 57 includes airfoils 59 which are in the core airflow path C. The turbines 46, 54 rotationally drive the respective low speed spool 30 and high speed spool 32 in response to the expansion. It will be appreciated that each of the positions of the fan section 22, compressor section 24, combustor section 26, turbine section 28, and fan drive gear system 48 may be varied. For example, gear system 48 may be located aft of combustor section 26 or even aft of turbine section 28, and fan section 22 may be positioned forward or aft of the location of gear system 48.

The engine 20 in one example is a high-bypass geared aircraft engine. In a further example, the engine 20 bypass ratio is greater than about six (6), with an example embodiment being greater than about ten (10), the geared architecture 48 is an epicyclic gear train, such as a planetary gear system or other gear system, with a gear reduction ratio of greater than about 2.3 and the low pressure turbine 46 has a pressure ratio that is greater than about five. In one disclosed embodiment, the engine 20 bypass ratio is greater than about ten (10:1), the fan diameter is significantly larger than that of the low pressure compressor 44, and the low pressure turbine 46 has a pressure ratio that is greater than about five 5:1. Low pressure turbine 46 pressure ratio is pressure measured prior to inlet of low pressure turbine 46 as related to the pressure at the outlet of the low pressure turbine 46 prior to an exhaust nozzle. The geared architecture 48 may be an epicycle gear train, such as a planetary gear system or other gear system, with a gear reduction ratio of greater than about 2.3:1. It should be understood, however, that the above parameters are only exemplary of one embodiment of a geared architecture engine and that the present invention is applicable to other gas turbine engines including direct drive turbofans.

A significant amount of thrust is provided by the bypass flow B due to the high bypass ratio. The fan section 22 of the engine 20 is designed for a particular flight condition—typically cruise at about 0.8 Mach and about 35,000 feet (10,668 meters). The flight condition of 0.8 Mach and 35,000 ft (10,668 meters), with the engine at its best fuel consumption—also known as "bucket cruise Thrust Specific Fuel Consumption ('TSFC')"—is the industry standard parameter of lbm of fuel being burned divided by lbf of thrust the engine produces at that minimum point. "Low fan pressure ratio" is the pressure ratio across the fan blade alone, without a Fan Exit Guide Vane ("FEGV") system. The low fan pressure ratio as disclosed herein according to one non-limiting embodiment is less than about 1.45. "Low corrected fan tip speed" is the actual fan tip speed in ft/sec divided by an industry standard temperature correction of $[(Tram\ °\ R)/(518.7°\ R)]^{0.5}$. The "Low corrected fan tip speed" as disclosed herein according to one non-limiting embodiment is less than about 1150 ft/second (350.5 meters/second).

Figure 1B:
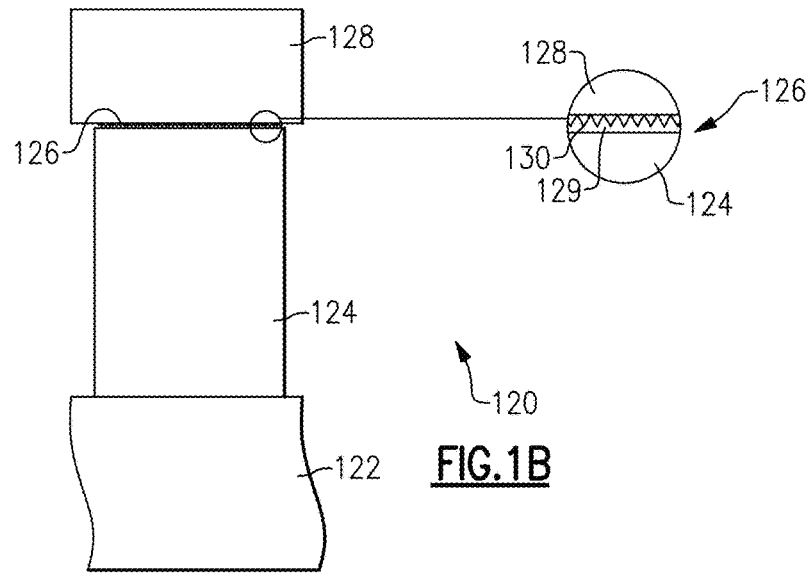
FIG. 1B shows a compressor blade.

FIG. 1B schematically shows a compressor blade row 120. A rotor 122 receives a plurality of blades 124 each having a radially outer tip 126 (only one shown). An abradable seal 128 is positioned outwardly of tip 126.

Shown in a detail, the blade 124 has a coating 129 on its outer tip 126 and there are abrasive particles 130 in that coating 129.

Example coatings could be cBN abrasive particles in a nickel matrix. Alternatively, aluminum oxide based abrasive grit may be utilized. Of course, many other abrasives may be utilized.

Figure 2A:
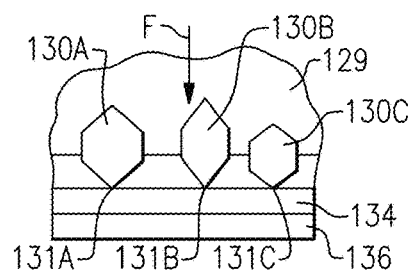
FIG. 2A shows a first step in a method.

FIG. 2A shows a method of inspecting whether recoating is required for the abrasive particles 130. As shown, the abrasive material is in particle form, such as 130A, 130B, and 130C. The particles are unworn and have pointed tips 131A, 131B, and 131C.

A marking paper 134 is placed to be contacted by the tips 131A, 131B, and 131C. A second piece of paper 136 is placed on the opposed side of the marking paper 134. A force F is applied, forcing the paper 134 against tips 131A, 131B, and 131C.

The marking paper may be similar to that known as articulating paper which is used for dentistry purposes. On the other hand, any media which passes an imprint from the tips 131A, 131B, and 131C or merely captures an imprint may be utilized. The term "marking paper" as utilized in this application should be interpreted to broadly cover any such media. One acceptable marking paper is available under the trade name Bausch Articulating Paper.

Figure 2B:
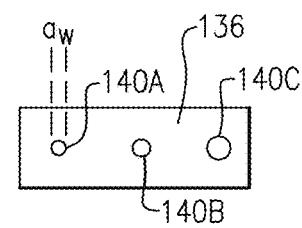
FIG. 2B shows a subsequent step.

Now, as shown in FIG. 2B, the second piece of paper 136 has small imprints 140A, 140B, and 140C from the marking paper 134. As shown, a contact diameter $a_w$ as associated with the mark 140A is relatively small. This is how the marks from an unworn blade or a blade that is not in need of recoating may appear.

Figure 2C:
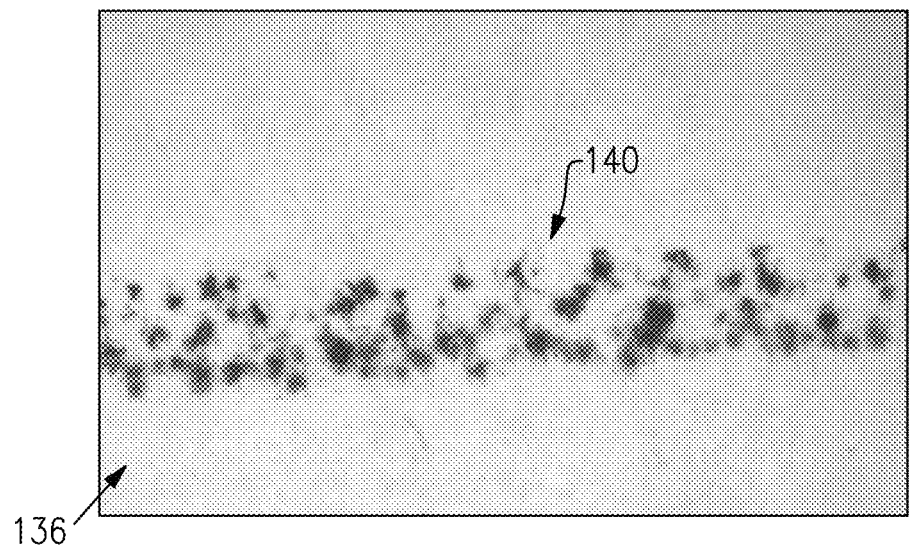
FIG. 2C is a more real world view of FIG. 2B.

FIG. 2C shows a more real world photograph of what the paper 136 may look like with a number of marks 140.

Figure 3A:
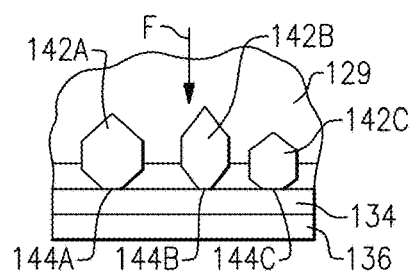
FIG. 3A shows another method step.
Figure 3B:
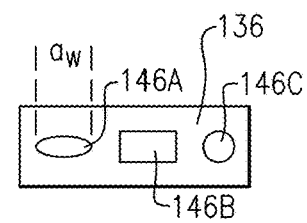
FIG. 3B shows a portion of a subsequent step.

FIG. 3A shows another occurrence of the method shown in FIG. 2A, however, now the abrasive particles 142A, 142B, and 142C have worn and may be in need of being recoated. The tips are no longer pointed, but rather as shown at 144A, 144B, and 144C, they are relatively flat. The force F is applied and the marks are formed on the paper 136 as shown in FIG. 3B. The marks can be seen to be much wider and cover a greater surface area as shown at 146A, 146B, and 146C compared to those in FIG. 2B. A contact width $a_w$ is shown to be much greater than that shown at $a_u$. The contact width is then correlated to the amount and percent wear of the tip.

Figure 3C:
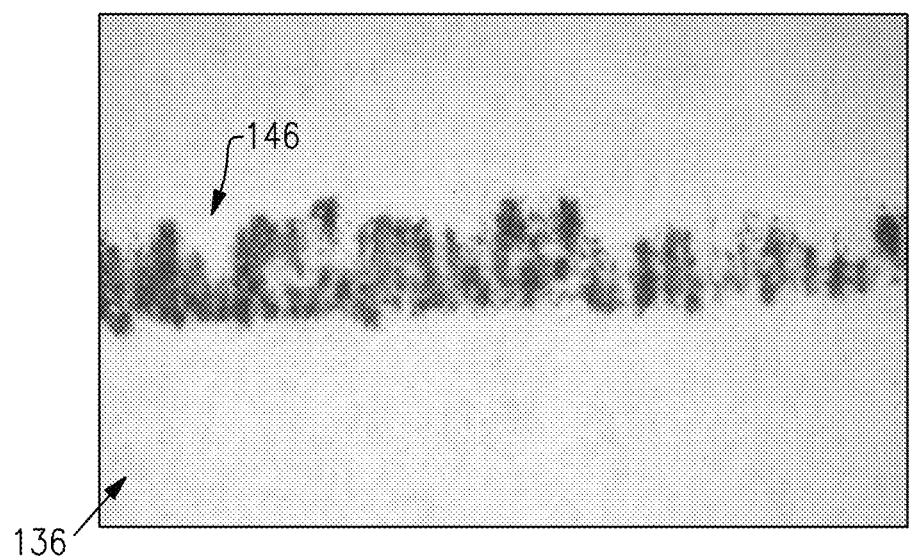
FIG. 3C is a more real world version of FIG. 3B.

FIG. 3C shows a real world example of the coverage of the marked area 146 from such a worn blade.

A decision can be made that recoating is in order based upon a review of the size of the marks, say, on average. The size may be compared to a limit and a need for recoating may be identified based upon that comparison.

Alternatively, the area of mark per area media may be compared to a limit to identify the need for recoating. As an example, by comparing FIG. 2C and FIG. 3C, it is evident that a greater surface area is covered by the marks 146 of the worn blade than of the mark 140 of the blade which is not in need of being recoated.

Figure 4A:
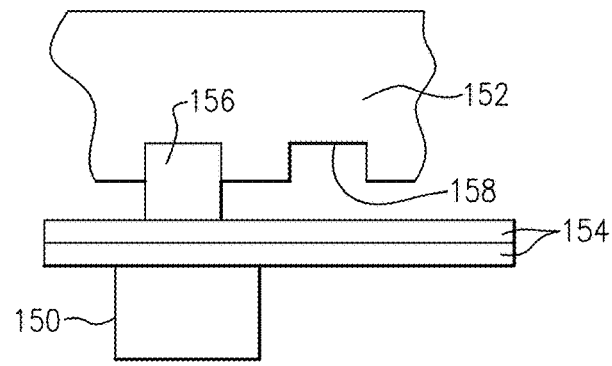
FIG. 4A shows another possible scenario.

FIG. 4A shows other potential features. As shown as in FIG. 4A, a gauge 150 may press the paper 154 against the blade 152. The gauge 150 will ensure a controllable force be applied to the paper to provide the contact force as described above. In addition, while particle 156 is shown in the blade 152, a void 158 where a particle may have been removed, may also be identified by this method. A missing particle would affect the percentage area, and thus the absence of particles is also identified as part of the quality determination.

Figure 4B:
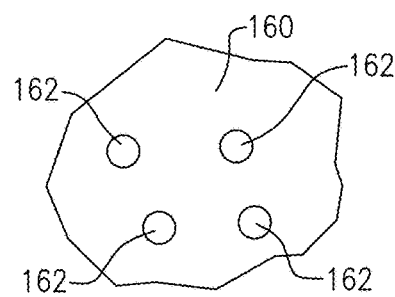
FIG. 4B shows yet another method embodiment.

FIG. 4B shows another embodiment. Here, the blade 160 has a number of particle chips 162. The marking paper will change the color of the chips 162, and rather than evaluating the size, or area on the paper, such can be done on the blade. Thus, the imprint of the media on the particles is evaluated to make the quality determination.

Figure 5:
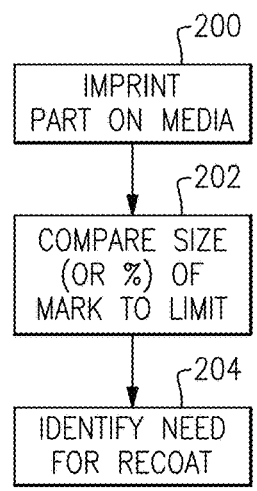
FIG. 5 shows a flowchart.

FIG. 5 is a flowchart of the method showing the steps of this disclosure. At step 200, an imprint of the blade is made on media. At step 202, the size, or the percentage area of mark, is compared to a limit. The media may be separate from the marking paper, as disclosed above, or the imprints may somehow be on the marking paper. At step 204, a need for recoating is identified based upon this comparison.

Thus, for purposes of this application, the "media" may be the marking paper 134 and separate paper 136 in combination, or alternatively just a piece of marking paper.

While the method is disclosed as a way of determining whether abrasive coating on a gas turbine engine blade must be recoated, it should be understood that the broad teachings of this disclosure could extend to testing the surface quality of any number of other components.

In addition, the method of this disclosure can be utilized to determine the quality of the coating after the coating has occurred.

Although an embodiment of this invention has been disclosed, a worker of ordinary skill in this art would recognize that certain modifications would come within the scope of this invention. For that reason, the following claims should be studied to determine the true scope and content of this invention.

The invention claimed is:

1. A method of evaluating the quality of a surface on a component comprising the steps of:
    (a) contacting a surface of a component with a media and imprinting qualities of the surface with the media to form an imprint;
    (b) evaluating the imprint to determine a quality of the surface of the component;
    wherein the surface of the component includes a plurality of particles and the evaluation includes determining whether the quality indicates the particles have worn such that they should be replaced; and
    wherein said component is a blade for a gas turbine engine and said media is a distinct element from said blade and said plurality of particles.

2. The method as set forth in claim 1, wherein the media includes a marking paper.

3. The method as set forth in claim 1, wherein a size of an average imprint is evaluated to determine whether the particles should be replaced.

4. The method as set forth in claim 1, wherein a percentage of mark per unit area is compared to a limit to identify whether the particles should be replaced.

5. The method as set forth in claim 1, wherein the particles are abrasive particles on a rotating blade in a gas turbine engine.

6. The method as set forth in claim 1, wherein an absence of particles is also identified as part of the quality determination.

7. The method as set forth in claim 1, wherein an imprint from the media on the particles is evaluated to make the quality determination.

8. The method as set forth in claim 1, wherein a gauge is utilized to ensure a controllable force provides a contact of step (a).

9. The method as set forth in claim 1, wherein the size of the average quality is evaluated to determine whether the particles should be replaced.

10. The method as set forth in claim 1, wherein a percentage of mark per unit area of the paper is compared to a limit to identify whether the particles should be replaced.

11. A method of evaluating the quality of a surface on a component comprising the steps of:
    (a) contacting a surface of a component with a media and imprinting qualities of the surface with the media to form an imprint, said component being a component in a gas turbine engine;
    (b) evaluating the imprint to determine a quality of the surface of the component;
    wherein the surface of the component includes a plurality of particles and the evaluation includes determining whether the quality indicates the particles have worn such that they should be replaced;
    wherein the media includes a marking paper; and
    the marking paper passes qualities from the surface onto a second piece of paper.

12. The method as set forth in claim 11, wherein a size of an average quality on the second paper is evaluated to determine whether the particles should be replaced.

13. The method as set forth in claim 11, wherein a percentage of mark on the second piece of paper per unit area of the paper is compared to a limit to identify whether the particles should be replaced.

14. The method as set forth in claim 11, wherein said component is a blade for the gas turbine engine.

15. The method as set forth in claim 11, wherein the particles are abrasive particles on a rotating blade in the gas turbine engine.

* * * * *